US011510561B2

(12) United States Patent
Rephaeli et al.

(10) Patent No.: US 11,510,561 B2
(45) Date of Patent: Nov. 29, 2022

(54) ENDOSCOPE DEFOGGING (71) Applicant: Verily Life Sciences LLC, Mountain View, CA (US)

(72) Inventors: Eden Rephaeli, Oakland, CA (US); Maximilian Kapczynski, Palo Alto, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 377 days.

(21) Appl. No.: 16/107,305

(22) Filed: Aug. 21, 2018

(65) Prior Publication Data
US 2020/0060537 A1 Feb. 27, 2020

(51) Int. Cl.
*A61B 1/12* (2006.01)
*A61B 1/002* (2006.01)
*A61B 1/00* (2006.01)

(52) U.S. Cl.
CPC .............. *A61B 1/127* (2013.01); *A61B 1/002* (2013.01); *A61B 1/0008* (2013.01); *A61B 1/00165* (2013.01)

(58) Field of Classification Search
None
See application file for complete search history.

(56) References Cited

U.S. PATENT DOCUMENTS

| 4,478,909 A * | 10/1984 | Taniguchi | B29D 11/00865 428/331 |
| 4,947,383 A * | 8/1990 | Hudson | G06K 17/0016 235/456 |
| 5,575,756 A * | 11/1996 | Karasawa | A61B 1/00068 600/121 |
| 5,605,532 A | 2/1997 | Schermerhorn | |
| 5,647,840 A * | 7/1997 | D'Amelio | A61B 1/00091 600/169 |
| 6,535,307 B1 * | 3/2003 | Allen | B41F 33/0036 358/406 |
| 6,749,427 B1 * | 6/2004 | Bretscher | A61B 1/247 433/30 |
| 6,868,190 B1 * | 3/2005 | Morton | G06T 5/00 348/208.13 |

(Continued)

FOREIGN PATENT DOCUMENTS

| DE | 102016007669 A1 | 12/2017 |
| JP | 6095418 A | 5/1985 |
| JP | 2003334157 A | 11/2003 |

OTHER PUBLICATIONS

International Search Report and Written Opinion dated Oct. 18, 2019 in corresponding International Patent Application No. PCT/US2019/046471, 23 pages.

*Primary Examiner* — John P Leubecker
*Assistant Examiner* — Jae Woo
(74) *Attorney, Agent, or Firm* — Christensen O'Connor Johnson Kindness PLLC (57) ABSTRACT

An endoscope includes a light source coupled to emit light, and a lens disposed proximate to a distal tip of the endoscope tube and structured to absorb at least some of the light. A controller is coupled to the light source, and the controller includes logic that when executed by the controller causes the endoscope to perform operations, including adjusting an emission profile of the light source to heat the lens with the light, and heating the lens mitigates formation of fog on the lens.

20 Claims, 5 Drawing Sheets

(56) References Cited

U.S. PATENT DOCUMENTS

| | | | | |
|---|---|---|---|---|
| 7,042,488 | B2* | 5/2006 | Higuchi | H04N 7/183 348/65 |
| 8,120,683 | B1* | 2/2012 | Turner | H04N 5/32 348/295 |
| 9,179,831 | B2* | 11/2015 | McGrail | A61B 1/00105 |
| 10,039,442 | B2* | 8/2018 | Otten | A61B 1/253 |
| 10,111,581 | B2* | 10/2018 | Makmel | H05B 3/84 |
| 10,244,932 | B2* | 4/2019 | Fujii | A61B 1/00163 |
| 10,303,961 | B1* | 5/2019 | Stoffel | B60Q 3/76 |
| 10,582,832 | B2* | 3/2020 | Lawrence | A61B 1/0607 |
| 10,890,910 | B1* | 1/2021 | Bart | G01K 19/00 |
| 2003/0076605 | A1* | 4/2003 | Shohet | A61B 1/247 359/840 |
| 2006/0069314 | A1* | 3/2006 | Farr | A61B 1/00096 600/179 |
| 2007/0149856 | A1* | 6/2007 | Segawa | A61B 1/127 600/169 |
| 2009/0202714 | A1* | 8/2009 | Mandzy | C09C 1/00 427/164 |
| 2010/0174144 | A1* | 7/2010 | Hsu | A61B 17/0469 600/122 |
| 2010/0222802 | A1* | 9/2010 | Gillespie, Jr. | A61F 2/2481 606/192 |
| 2013/0116507 | A1* | 5/2013 | Segawa | A61B 1/128 600/109 |
| 2013/0303853 | A1* | 11/2013 | Takahashi | A61B 1/0051 600/134 |
| 2013/0310644 | A1* | 11/2013 | Ichimura | A61B 1/00096 600/109 |
| 2014/0005484 | A1* | 1/2014 | Charles | A61B 1/00149 600/201 |
| 2014/0088366 | A1 | 3/2014 | Solingen | |
| 2014/0200406 | A1* | 7/2014 | Bennett | A61B 1/0646 600/109 |
| 2014/0272765 | A1* | 9/2014 | Andreiko | A61B 1/00006 433/27 |
| 2014/0288370 | A1* | 9/2014 | Jungbauer | A61B 1/053 600/112 |
| 2015/0173591 | A1* | 6/2015 | Zheng | A61B 1/0684 600/169 |
| 2015/0201826 | A1* | 7/2015 | Hsu | A61B 1/00135 600/121 |
| 2015/0223672 | A1* | 8/2015 | Otten | A61B 1/253 600/169 |
| 2015/0289751 | A1* | 10/2015 | Frerck | B08B 17/065 600/121 |
| 2016/0081541 | A1* | 3/2016 | Yasue | A61B 1/127 600/169 |
| 2016/0113484 | A1* | 4/2016 | Nakaguchi | A61B 1/00048 600/103 |
| 2016/0262856 | A1* | 9/2016 | Atiya | A61B 1/015 |
| 2017/0100024 | A1* | 4/2017 | Shahmoon | G02B 23/26 |
| 2017/0226371 | A1* | 8/2017 | Deshpande | C09D 133/14 |
| 2019/0136070 | A1* | 5/2019 | Aizenberg | A61B 1/018 |
| 2019/0340940 | A1* | 11/2019 | Elkabetz | G08G 5/0091 |
| 2019/0385025 | A1* | 12/2019 | McMichael | G06K 9/00791 |
| 2020/0060537 | A1* | 2/2020 | Rephaeli | A61B 1/07 |
| 2020/0077869 | A1* | 3/2020 | Ida | G06T 5/50 |
| 2020/0337537 | A1* | 10/2020 | Hirasawa | G06T 7/0012 |

* cited by examiner

ENDOSCOPE DEFOGGING

TECHNICAL FIELD

This disclosure relates generally to surgical technologies, and in particular, relates to endoscope-assisted surgery.

BACKGROUND INFORMATION

Endoscopy allows a physician to view organs and cavities internal to a patient using an insertable instrument. This is a valuable tool for making diagnoses without needing to guess or perform exploratory surgery. The insertable instruments, sometimes referred to as endoscopes or borescopes, have a portion, such as a tube, that is inserted into the patient and positioned to be close to an organ or cavity of interest.

Endoscopes first came into existence in the early 1800's, and were used primarily for illuminating dark portions of the body (since optical imaging was in its infancy). In the late 1950's, the first fiber optic endoscope capable of capturing an image was developed. A bundle of glass fibers was used to coherently transmit image light from the distal end of the endoscope to a camera. However, there were physical limits on the image quality this seminal imaging endoscope was able to capture: namely, the number of fibers limited the resolution of the image, and the fibers were prone to breaking.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of an apparatus and method for endoscope defogging are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The condensation of water on the optical window of endoscopes (aka fogging) is a big nuisance in many surgical procedures. Fog reduces the visibility of the surgical scene, which has a direct implication on the safety and viability of the surgical procedure.

In general, fogging results when the endoscope's window (i.e., an optically clear element providing a seal between the surgical scene and the interior of the endoscope; which may be made of sapphire due to its strength) temperature is lower than the dew-point temperature of the air or gas in the surgical volume (e.g., insufflated abdomen), thus leading to condensation of water.

Unfortunately, for the patient, mitigation of fogging usually requires removal of the endoscope and wiping it with a cloth, a process which has to be repeated every few minutes, and disrupts the surgical procedure. Other solutions include using forced convection by flowing air on the endoscope window. However, this solution adds bulk to the endoscope (specifically the diameter of the endoscope increases), and is therefore not an option in most cases. Additionally, this solution requires coupling air or some other gas into flow channels, adding complexity in setup and usage. As a consequence, despite the great desire on the part of clinicians to reduce fogging, there is no satisfying solution for this problem, thus creating a clear need for innovation.

Embodiments disclosed herein present a solution to the fogging problem using selective absorption of light. Specifically, in some embodiments, an endoscope cover window may be fabricated from an optically clear material, that is doped with metal nanoparticles, nanorods, or metal-dielectric nanoparticles or nanorods. When one or more dimensions of a metal are sufficiently small (typically in the sub-micron range), the absorption of the metal can be tuned across the visible and near-infrared (NIR) spectrum by tuning this small dimension. Due to symmetry considerations, nanosphere absorption is less polarization-sensitive, while nanorods can be made to selectively absorb a certain polarization of light. The resulting absorption peaks can be 10's of [nm] in width, which does not pose problem for this scheme.

In other embodiments, the endoscope lens may be made from an optically clear material that is coated on the inside of the lens with a thin-film designed to maximize absorption at a specific wavelength (e.g., a "heating wavelength" $\lambda_h$). Thin film coatings can be designed with absorption peaks as narrow as 1 [nm]. This coating can also be combined with a fluorescence notch filter, which may be used for performing fluorescence imaging. The coating can alternatively be deposited on the outside of the cover lens and combined with an anti-reflective coating.

Light absorbed by either one of the ways described above would then heat up the optical lens, and would allow tuning of the lens's temperature to minimize or eliminate fogging.

Fiber bundle (e.g., fibers in the endoscope tube) based illumination may be used to provide light to illuminate the scene for imaging, and also transmit light (from either laser, LEDs, lamps, or the like), in the wavelength corresponding to an absorption peak in the cover window, stemming from one of the two mechanisms described above. Since typical fiber bundles used for illumination transmit light in the range of 400-1700 nm, it is possible to pick $\lambda_h$ to be either outside of the sensitivity range of the image sensor (typically 400-1100 nm for silicon), or in some wavelength band that can be blocked off somewhere inside the optics barrel of the endoscope, thus eliminating the possibility the light at $\lambda_h$ will cause image quality artifacts or otherwise interfere with the imaging process.

A light source may be used containing the heating wavelength $\lambda_h$, that can couple light into the fiber bundle. One implementation combining some imaging modality requiring polarized light (such as speckle flow imaging, or optical coherence tomography), could use the same $\lambda_h$ to heat up the optical window of the endoscope by designing a coating or doping scheme that absorbs one polarization, thus allowing the other polarization at $\lambda_h$ to be used for coherent illumination.

With the implementations described above, in an endoscope architecture, light in the heating wavelength $\lambda_h$ can be pulse on and off, either upon user button press or periodically following some experimentally-validated pulse scheme shown to provide effective de-fogging and otherwise minimizing light power.

In some embodiments, the heating wavelength $\lambda_h$ can be pulse on and off based on a feedback algorithm performing an analysis of the endoscope video stream to detect the presence and/or severity of fogging, where more fogging will result in high power from the light source at $\lambda_h$, either in the instantaneous power sense or in the time-averaged sense. This algorithm can be based on machine learning, where the algorithm is trained on a set of images devoid of fog, and ones with fog present. The algorithm output can be binary (indicating whether fog is present or not), or could output a scalar taking on continuous values in some specified range which would correspond to the severity of fogging. In some embodiments, an algorithm could calculate a measure of resolution in real-time. This algorithm can be based on detecting edges in the scene (which may be part of a demosaicking algorithm and likely part of the camera image processing pipeline), and estimating from those the modulation transfer function (MTF) of the system. It would then infer the presence of fog by detecting degradation in the MTF during surgery. This algorithm can be experimentally tuned by exposing the endoscope to fog and mapping the severity of fog to a variable related to the MTF.

One aim of the algorithm, at a high-level, is to raise the temperature of the optical window above the dew point temperature. The temperature conditions required to prevent fogging may differ from those required to eliminate fogging once it is already present (mostly due to the latent heat required to induce evaporation). Accordingly, different modes of operation and different algorithm response at different times may be necessary.

The following disclosure will describe the embodiments discussed above, in addition to other embodiments, as they relate to the figures.

Figure 1:
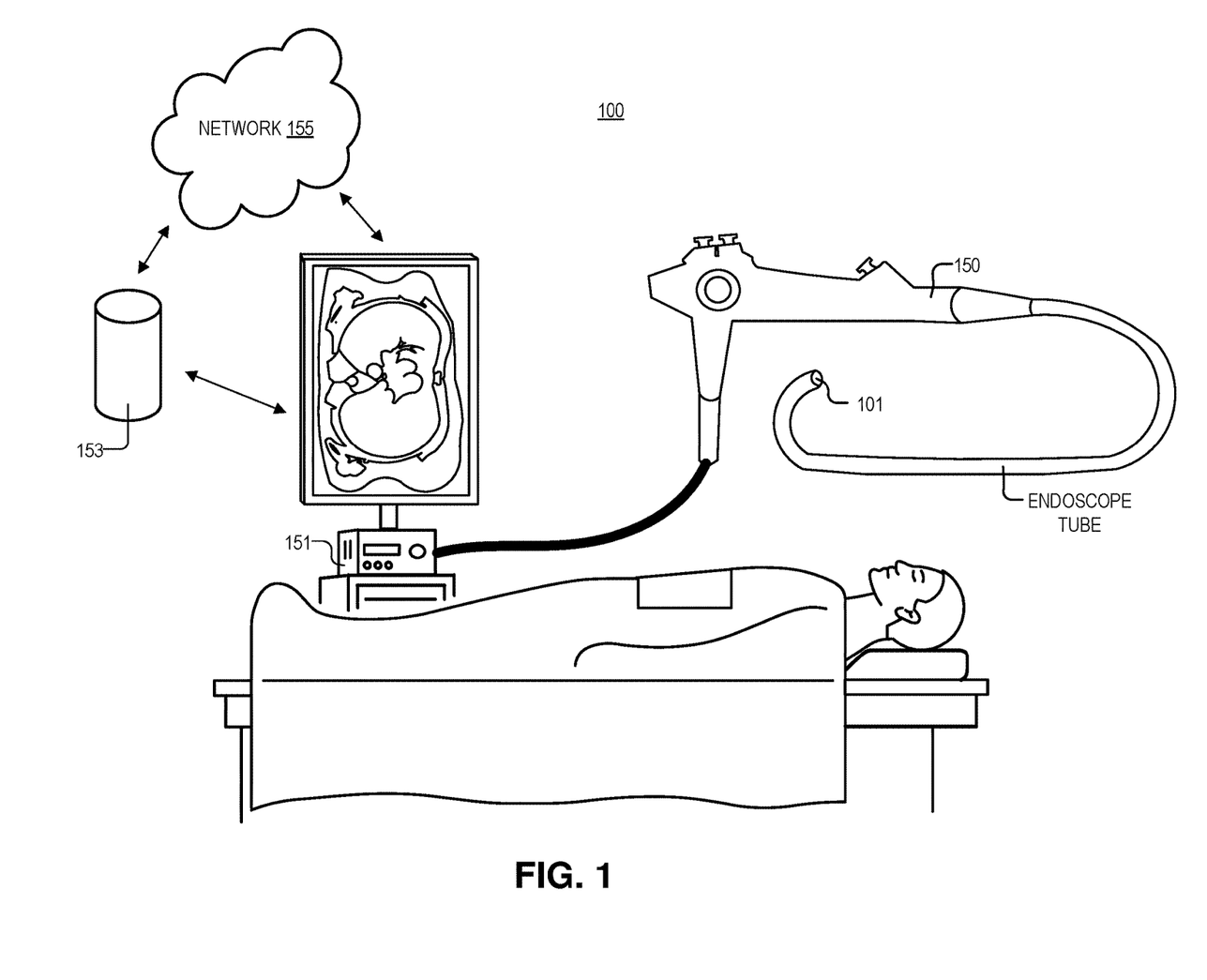
FIG. 1 illustrates an endoscope system, in accordance with an embodiment of the present disclosure.

FIG. 1 illustrates an endoscope system 100, in accordance with an embodiment of the present disclosure. Endoscope system 100 includes endoscope 150 (with distal tip 101), computer 151, storage 153, and network 155. It is appreciated that the endoscope controller may include elements of computer 151, storage 153, and network 155 as well as control circuitry and software contained in endoscope 150. Put another way, the controller may be a distributed system where different processes occur in different locations (e.g., in endoscope 150, in computer 151, and/or on remote servers), in accordance with the teachings of the present disclosure. As shown, all components depicted are coupled by wires or wirelessly.

In some embodiments, network 155 and storage 153 may run algorithms (like machine learning algorithms) and perform image processing. Computer 151 may also handle some amount of image processing, communicate with storage 153/network 155, and control various operational aspects of endoscope 150 (e.g., the amount of light output from distal tip 101, contrast of the image received from the camera, or the like).

As shown, the proximal (hand-held) end of endoscope may have a number of buttons and joysticks to control the movement of distal tip 101. One of ordinary skill in the art will appreciate that endoscope 150 depicted here is merely a cartoon illustration of an endoscope, and that the term "endoscopy" should encompass all types of endoscopy (e.g., laparoscopy, endoscopy, robotic surgery, or any other situation when a camera is inserted into a body), and that an endoscope should include at least "chip-on-a-tip" devices, rod lens devices (ridged), image fiber devices (flexible) to name a few. Endoscope 150 may be included in surgical robotic systems or coupled to a surgical robot.

Figure 2A:
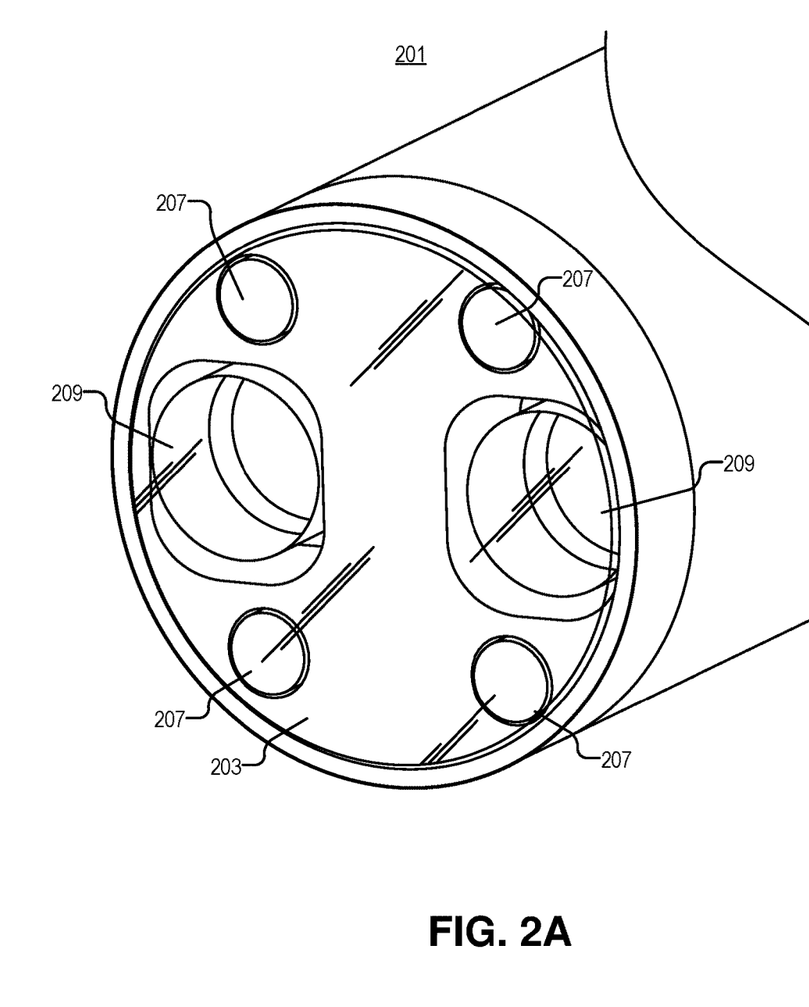
FIG. 2A illustrates a first view of a distal tip of the endoscope depicted in FIG. 1, in accordance with an embodiment of the present disclosure.

FIG. 2A illustrates a first view of the distal tip 201 of the endoscope tube depicted in FIG. 1, in accordance with an embodiment of the present disclosure. Specifically, the depicted embodiment shows the distal tip of a "chip-on-a-tip" stereo laparoscope, however, one of ordinary skill will appreciate that the techniques described here apply to other endoscope systems. As illustrated, light source 207 (e.g., light emitting diodes, laser diodes, the ends of optical fiber(s) to transmit light from a remote source) is coupled to emit light, and lens 203 (e.g., which may, or may not, have optical power and include sapphire, glass, or the like) is disposed proximate to distal tip 201 of the endoscope. Lens 203 is structured to absorb at least some of the light. A controller (e.g., including a general purpose processor, application specific integrated circuit, distributed system, memory, or the like) is coupled to light sources 207, and the controller includes logic that when executed by the controller causes the endoscope to perform operations. The operations may include adjusting an emission profile of light sources 207 to heat lens 203 with the light, and, as stated above, heating lens 203 mitigates formation of fog (condensation) on lens 203.

As shown, distal end 201 includes at least one camera 209 (e.g., image sensors, or fiber optics to send the image back to a camera in the proximal end of the endoscope) optically coupled to receive image light (e.g., light from the body/patient) through lens 203. Once the image light is received, cameras 209 may convert the image light into image data, and send the image data to the controller. The controller may detect a presence of the fog on the lens using the image data (e.g., using at least one of a modular transfer function or a machine learning algorithm running on the controller). And, in response to detecting the presence of the fog the controller may adjust the emission profile (e.g., an intensity, a duty ratio, or a wavelength) of the light source to heat the lens. It is appreciated that lens 203 is structured (e.g., with texturing, inclusions, a film disposed on the lens, or the like) to absorb a non-visible portion of the light (e.g., infrared light with a wavelength between 2000 nm and 1100 nm—light outside of the absorption spectrum of cameras 209). It is appreciated that in most embodiments, the lens is optically transparent to a majority of visible light wavelengths (so image light can pass through unimpeded). In the depicted example, two cameras 209 are present in the endoscope (e.g., for stereo viewing), but in other examples a single camera may be employed. As shown, lens 203 may form a seal with the housing of the endoscope tube (e.g., including electronic connections, fiber optic cables, actuators, or the like) to prevent moisture from reaching the electronic and optical components disposed behind lens 203.

In some embodiments, the emission profile of light source 207 when the fog is present on lens 203 is different than the emission profile of light sources 207 when the fog is not present on lens 203. As stated above, this may be due to differences in the physics of water already droplets already being present on the lens (e.g., having to contend with the latent heat of vaporization), vs. water droplets trying to condense on the lens. In some embodiments, light sources 207 may be independently controlled to create different heat gradients and profiles across the surface of lens 203 depending on how lens 203 is fogging. The various algorithms analyzing the video feed may determine where and how much to heat lens 203 (e.g., create a linear, normal, parabolic, or the like heat distribution across lens 203 with the hottest part of lens 203 being an area that is fogging). In some embodiments, the lens is heated only in the places that are fogging. In another or the same embodiment, a baseline heating is applied to the entire lens 203 (to prevent fogging), and the heat/light intensity is increased in locations on lens 203 where fogging starts to occur. In some embodiments, the controller (or software on the controller) may automatically correct image distortion in the video data that is caused by lens expansion/contraction due to heating.

Figure 2B:
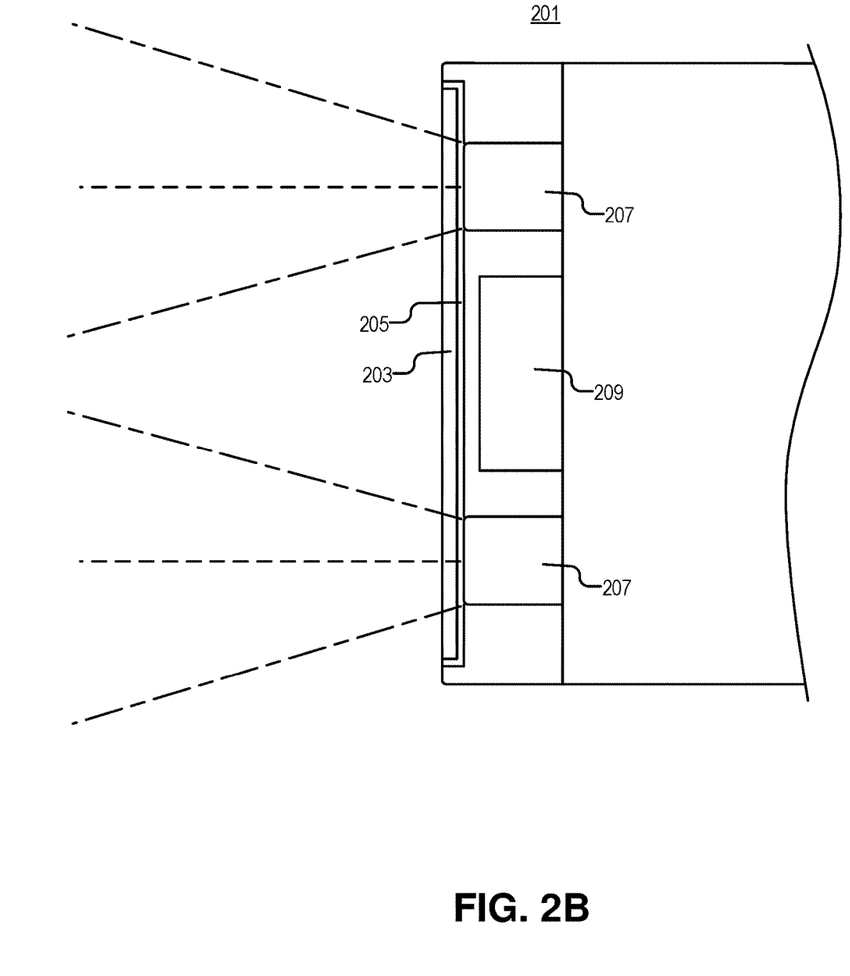
FIG. 2B illustrates a second view of the distal tip of the endoscope depicted in FIG. 1, in accordance with an embodiment of the present disclosure.

FIG. 2B illustrates a second view of the distal end 201 of the endoscope depicted in FIG. 1, in accordance with an embodiment of the present disclosure. However, here, in the cross sectional view, film 205 is shown. In the depicted example, film 205 is disposed on a side of lens 203 proximate to the light sources 207. Film 205 is structured to absorb at least some of the light and heat lens 203. This may be achieved by including at least one of metal nanoparticles, metal nanorods, metal-dielectric nanoparticles, or metal-dielectric nanorods in film 205. One of skill in the art will appreciate that the size of these structures may be tuned to absorb specific wavelengths of light. In other or the same embodiments, quantum dots, small molecule organic and inorganic dyes may also be used. In some embodiments, film 205 may have an infrared absorption spectrum that facilitates heating or may be textured to produce heating. In some embodiments, film 205 is a polymer matrix, a glass matrix, or other oxide matrix (e.g., sol-gel precursor based matrix), with the particles disposed within. In some embodiments, lens 203 itself may include inclusions/particles or be textured to produce heating.

Figure 3:
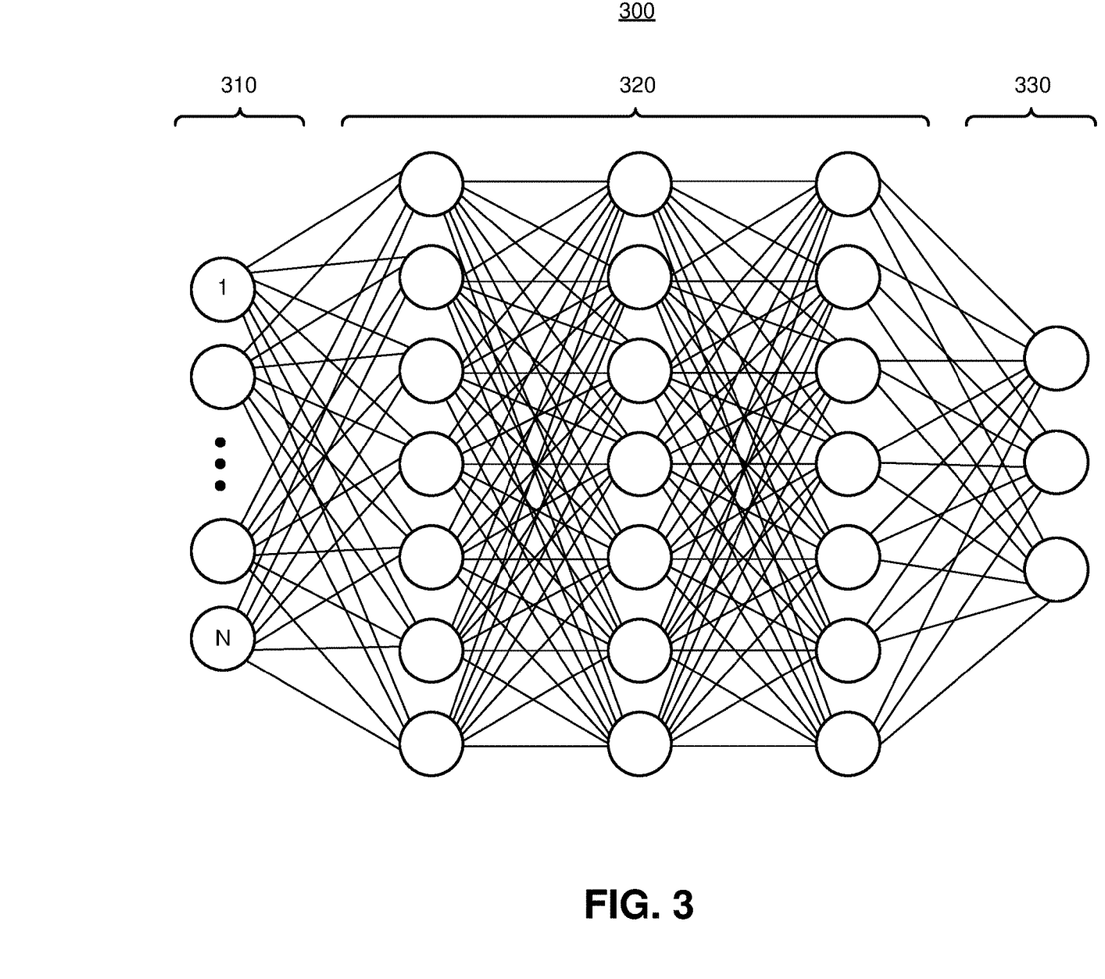
FIG. 3 is a graphical depiction of a machine learning algorithm that may run on the system of FIG. 1, in accordance with an embodiment of the present disclosure.

FIG. 3 is a graphical depiction of machine learning algorithm 300 that may run on the system of FIG. 1, in accordance with an embodiment of the disclosure. Machine learning algorithm 300 includes an input layer 310, an output layer 330, and multiple hidden layers 320 disposed between the input layer 310 and the output layer 330. The number of nodes in input layer 310 may be dependent on the inputs (e.g., the number of video feeds), and output layer 330 may output the data describing the intensity of light output needed to prevent fogging. In some embodiments, the number of input nodes is related to the number of various inputs and their particular resolution. It is appreciated that multiple machine learning algorithms like the one depicted may be running (and trained) separately for each input (e.g., the type of image that each image sensor captures). The weight distribution for the connections between nodes is not illustrated, but it is appreciated that the specific values are highly dependent on the training or pre-training method, the number of training iterations (e.g., number of training samples) performed, to name a few.

The type of neural network utilized for the machine learning algorithm 300 is highly configurable and dependent on the inputs and the data being analyzed. Thus, in some embodiments, the machine learning model 300 may utilize deep learning like radial basis function neural network, a recurrent neural network, long-short term memory network, a convolution neural network, a modular neural network, or other types of neural networks. As described above, machine learning algorithm 300 may be used in conjunction (e.g., at the same time or in some sequential order) with other algorithms (e.g., analysis of a modular transfer function) to generate the light output requirements, in accordance with the teachings of the present disclosure.

Figure 4:
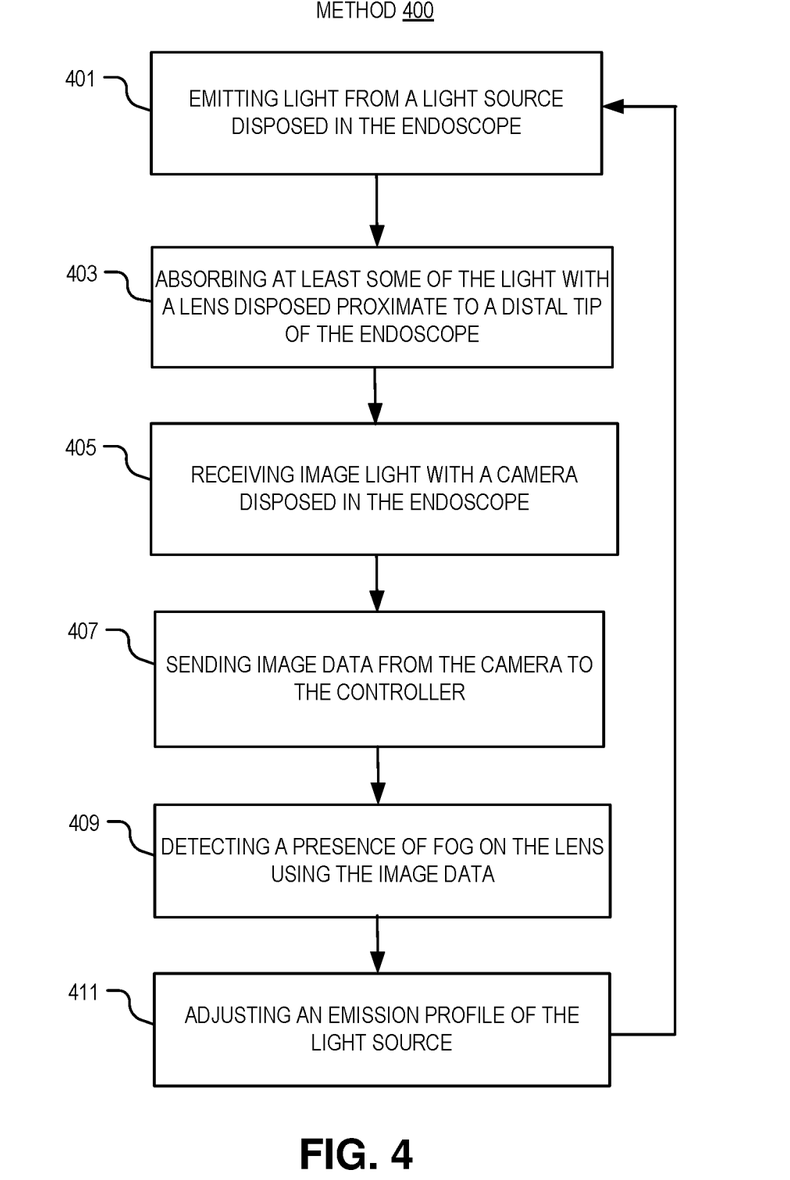
FIG. 4 illustrates a method of endoscopy, in accordance with an embodiment of the present disclosure.

FIG. 4 illustrates a method 400 of endoscope operation, in accordance with an embodiment of the disclosure. One of ordinary skill in the art having the benefit of the present disclosure will appreciate that the order of blocks (401-409) in method 400 may occur in any order or even in parallel. Moreover, blocks may be added to, or removed from, method 400 in accordance with the teachings of the present disclosure.

Block 401 shows emitting light from a light source disposed in the endoscope. As stated this may include emitting light in the infrared, near infrared, visible, and ultraviolet ranges. It is appreciated that the wavelength of light emitted depends on the absorption spectrum of the lens. Emitting light from the light source may include first sending at least some of the light from the light source through a film on the lens and then sending the light through the lens (after sending the light through the film). Put another way, the film is disposed between the light source and the lens.

Block 403 illustrates absorbing at least some of the light with a lens, where the lens is structured to absorb at least some of the light to heat the lens. As stated, structuring the lens may include using absorptive coatings, including absorptive defects in the lens material, texturing the surface of the lens/film, or the like. Absorbing at least some of the light may include absorbing a non-visible portion of the light, and passing a majority of visible light wavelengths through the lens.

Block 405 shows receiving image light with a camera disposed in the endoscope. The camera may be a CMOS image sensor or other digital camera which absorbs visible and nonvisible light. It is appreciated that notch filters may be employed with the heating lens disclosed herein. Notch filters may be used to exclude excitation light wavelengths (e.g., emitted from the light source) used in conjunction with florescent dyes in various dye-enhanced surgeries.

Block 407 shows sending image data from the camera to the controller. This may be achieved via a wired or wireless connection, and may include transferring information to the internet or other network.

Block 409 illustrates detecting a presence of the fog on the lens using the image data. As stated above, this may be achieved with deep learning models trained to recognize fog, or may be achieved with other logic such as modular transfer functions that can uniquely identify when the image is obstructed with fog on the lens.

Block 411 describes adjusting, using a controller coupled to the light source, an emission profile of the light source. Adjusting an emission profile may include adjusting at least one of an intensity, a duty ratio, a wavelength, or the like. Mitigation may include reducing the presence of fog already on the lens, or preventing fog form forming on the lens. It is appreciated that the emission profile of the light source when the fog is present on the lens may be different than the emission profile of the light source when the fog is not present on the lens.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine or controller (e.g., a computer, network device, personal digital assistant, manufacturing tool, any device with a set of one or more processors, general-purpose processor configured by firmware/software, programmable gate array, or application specific integrated circuit, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An endoscope, comprising:
    an endoscope tube;
    a light source optically coupled to the endoscope tube to emit light through the endoscope tube towards a distal tip of the endoscope tube;
    a lens disposed proximate to the distal tip of the endoscope tube to receive the light and structured to absorb at least some of the light when the light includes a heating wavelength, and wherein the lens is optically transparent to a majority of visible light wavelengths;
    a camera coupled to the endoscope tube to receive image light through the lens; and
    a controller coupled to the light source and the camera, wherein the controller includes logic that when executed by the controller causes the endoscope to perform operations, including:
        receiving image data from the camera, wherein the image data is representative of the image light;
        detecting, with a machine learning algorithm included in the logic of the controller, a presence of fog on the lens based on the image data;
        detecting edges of a scene included in the image data;
        estimating a modulation transfer function (MTF) of the endoscope based on the edges;
        outputting a variable related to the MTF representative of a severity of the fog based on a change in the MTF; and
        in response to detecting the presence of the fog, adjusting an emission profile of the light source to heat the lens by absorption of the at least some of the light to reduce the fog on the lens.

2. The endoscope of claim 1, wherein the lens includes at least one of metal nanoparticles, metal nanorods, metal-dielectric nanoparticles, or metal-dielectric nanorods to structure the lens to absorb the at least some of the light, wherein the at least some of the light is a non-visible portion of the light.

3. The endoscope of claim 1, wherein the lens includes a film disposed on the lens, and the film is structured to absorb the at least some of the light for heating the lens.

4. The endoscope of claim 3, wherein the film is disposed on a side of the lens proximate to the light source.

5. The endoscope of claim 3, wherein the film includes at least one of metal nanoparticles, metal nanorods, metal-dielectric nanoparticles, or metal-dielectric nanorods to structure the lens to absorb the at least some of the light.

6. The endoscope of claim 1, wherein the logic causes the emission profile of the light source when the fog is present on the lens to be different than the emission profile of the light source when the fog is not present on the lens.

7. The endoscope of claim 1, wherein adjusting the emission profile includes adjusting at least one of an intensity of the light, a duty ratio of the light source, or a wavelength of the light emitted by the light source.

8. The endoscope of claim 1, wherein the lens includes sapphire.

9. The endoscope of claim 1, wherein the machine learning algorithm included in the logic is a neural network.

10. The endoscope of claim 1, wherein the machine learning algorithm is trained to detect the fog with a first set of images devoid of fog and a second set of images inclusive of fog.

11. The endoscope of claim 1, wherein the adjusting the emission profile of the light source is based on the severity of the fog.

12. A method of endoscope operation, comprising:
    emitting light from a light source disposed in the endoscope;
    absorbing at least some of the light with a lens disposed proximate to a distal tip of an endoscope tube of the endoscope to receive the light and, wherein the lens is structured to absorb at least some of the light when the light includes a heating wavelength to heat the lens;
    receiving image data from a camera coupled to the endoscope tube to receive image light through the lens, wherein the image data is representative of the image light;
    detecting, with a machine learning algorithm, a presence of fog on the lens based on the image data;
    detecting edges of a scene included in the image data;
    estimating a modulation transfer function (MTF) of the endoscope based on the edges;
    outputting a variable related to the MTF representative of a severity of the fog based on a change in the MTF; and
    in response to detecting the presence of the fog, adjusting an emission profile of the light source to heat the lens by absorption of the at least some of the light to reduce the fog on the lens.

13. The method of claim 12, wherein absorbing the at least some of the light includes absorbing a non-visible portion of the light, and passing a majority of visible light wavelengths through the lens.

14. The method of claim 12, wherein absorbing the at least some of the light includes using a film disposed on the lens, and the film is structured to absorb the at least some of the light for heating the lens.

15. The method of claim 14, wherein emitting the light from the light source includes transmitting at least a portion of the light from the light source through the film and then through the lens.

16. The method of claim 14, wherein absorbing the at least some of the light includes using at least one of metal nanoparticles, metal nanorods, metal-dielectric nanoparticles, or metal-dielectric nanorods_sized to absorb the at least some of the light.

17. The method of claim 12, wherein the emission profile of the light source when the fog is present on the lens is different than the emission profile of the light source when the fog is not present on the lens.

18. The method of claim 12, wherein adjusting the emission profile includes adjusting at least one of an intensity of the light, a duty ratio of the light source, or a wavelength of the light emitted by the light source.

19. The method of claim 12, wherein emitting the light includes transmitting at least some of the light through sapphire.

20. The method of claim 12, wherein the adjusting the emission profile of the light source is based on the severity of the fog.

* * * * *

UNITED STATES PATENT AND TRADEMARK OFFICE
CERTIFICATE OF CORRECTION

PATENT NO. : 11,510,561 B2
APPLICATION NO. : 16/107305
DATED : November 29, 2022
INVENTOR(S) : E. Rephaeli et al.

Page 1 of 1

It is certified that error appears in the above-identified patent and that said Letters Patent is hereby corrected as shown below:

In the Claims

| Column | Line | |
|---|---|---|
| 9 | 14 | Claim 16, change "nanorods_sized" to -- nanorods sized --. |

Signed and Sealed this
Twenty-seventh Day of June, 2023

Katherine Kelly Vidal
*Director of the United States Patent and Trademark Office*